(12) United States Patent
Youssefirad

(10) Patent No.: US 10,589,031 B2
(45) Date of Patent: Mar. 17, 2020

(54) FLEXIBLE MEDICAMENT INJECTOR AND METHOD OF USE

(71) Applicant: Marie Youssefirad, Port Townsend, WA (US)

(72) Inventor: Marie Youssefirad, Port Townsend, WA (US)

( * ) Notice: Subject to any disclaimer, the term of this patent is extended or adjusted under 35 U.S.C. 154(b) by 138 days.

(21) Appl. No.: 15/072,082

(22) Filed: Mar. 16, 2016

(65) Prior Publication Data

US 2017/0266383 A1 Sep. 21, 2017

(51) Int. Cl.
*A61M 5/31* (2006.01)
*A61M 5/315* (2006.01)
*A61D 7/00* (2006.01)
*A61M 5/158* (2006.01)

(52) U.S. Cl.
CPC .............. *A61M 5/3134* (2013.01); *A61D 7/00* (2013.01); *A61M 5/3129* (2013.01); *A61M 5/3135* (2013.01); *A61M 5/31566* (2013.01); *A61M 5/31511* (2013.01); *A61M 2005/1586* (2013.01); *A61M 2205/586* (2013.01); *A61M 2250/00* (2013.01)

(58) Field of Classification Search
CPC .......... A61M 25/02–25/04; A61M 2005/1586; A61M 3/027; A61M 5/3134; A61M 5/3137; A61M 5/345; A61M 25/0637; A61M 5/28–5/288; A61M 5/158; A61M 4/3134; A61M 5/3129; A61M 5/31566; A61M 5/31511; A61M 2205/586; A61M 2250/00; A61M 5/3135; Y10S 128/26; A61D 7/00
See application file for complete search history.

(56) References Cited

U.S. PATENT DOCUMENTS

| 4,161,177 | A | * | 7/1979 | Fuchs | A61M 25/0637 604/164.01 |
|---|---|---|---|---|---|
| 4,769,011 | A | * | 9/1988 | Swaniger | A61F 2/4601 604/218 |
| 6,231,548 | B1 | * | 5/2001 | Bassett | A61M 25/02 128/DIG. 26 |
| 7,077,826 | B1 | * | 7/2006 | Gray | A61M 5/3135 604/171 |
| 7,118,378 | B1 | * | 10/2006 | Karapetyan | A61C 8/0009 433/90 |
| 2008/0009823 | A1 | * | 1/2008 | McKay | A61B 17/7044 604/500 |

* cited by examiner

Primary Examiner — Brandy S Lee
(74) Attorney, Agent, or Firm — Perkins Coie LLP

(57) ABSTRACT

An injector device and method for use, and particularly a veterinary injector, is disclosed herein. One aspect of the present technology, for example, is directed toward a veterinary injector including a flexible container configured to house a medicament, a plunger configured to be slidably received within a lumen of the container, a needle, and a stabilizer at the distal portion of the container and configured to be grasped by a user. The stabilizer can include a first flap extending away from the hub in a first direction, a second flap extending away from the hub in a second direction, and a third flap extending away from the hub in a third direction.

17 Claims, 1 Drawing Sheet

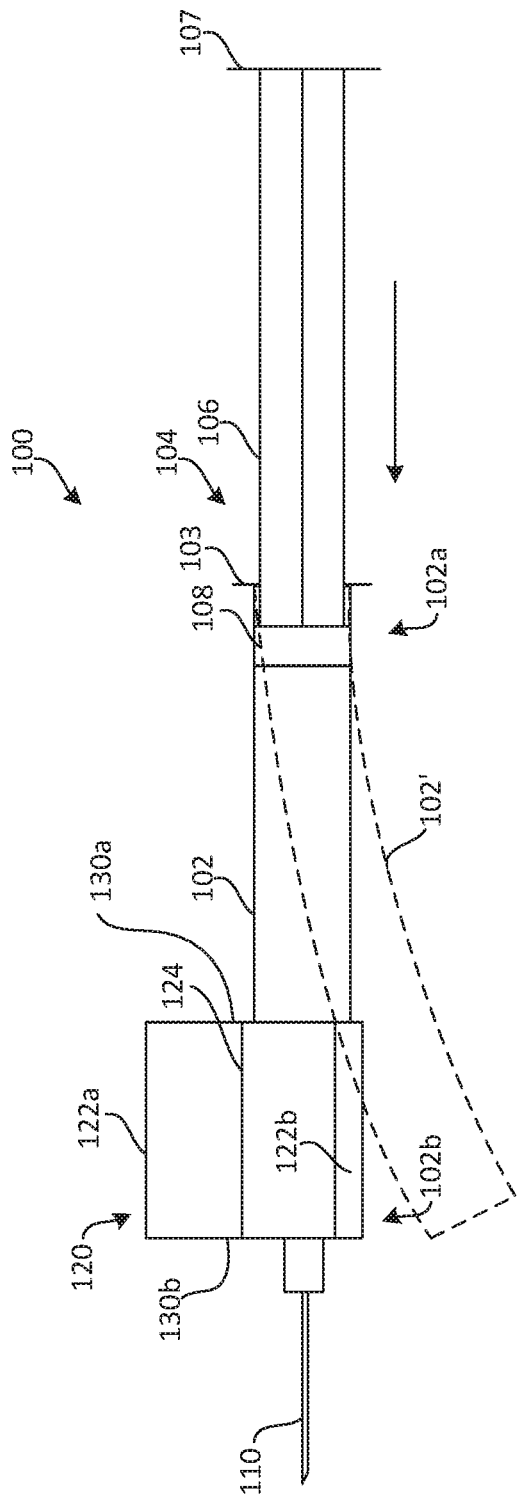

FLEXIBLE MEDICAMENT INJECTOR AND METHOD OF USE

TECHNICAL FIELD

The present technology is directed generally to flexible medicament injectors and associated devices, systems, and methods. Many embodiments of the present technology relate to veterinary medicament injectors.

BACKGROUND

Administering a dose of medicine to an animal can be particularly difficult, especially if the medicine is to be administered with a needle. Even domesticated animals are unlikely to hold still while the needle is positioned under their skin and the medicine is injected, making it very difficult for a single person to administer the medication. Often times, two people are required; one to restrain the animal, and the other to deliver the medication. The rigidity of conventional syringes make the process even more difficult, especially once the needle is positioned under the skin. Accordingly, there remains a need for improved medicament injectors and methods of use.

BRIEF DESCRIPTION OF THE DRAWINGS

FIG. 1 is a side view of an injector configured in accordance with an embodiment of the present technology.

FIG. 2 is an isolated, end view of a stabilizer configured in accordance with an embodiment of the present technology.

FIG. 3 is an isolated, end view of a stabilizer configured in accordance with another embodiment of the present technology.

DETAILED DESCRIPTION

FIG. 1 is a side view of a flexible injector 100 configured in accordance with the present technology. As shown in FIG. 1, the injector 100 can include a flexible medicament container 102 having a proximal portion 102a, a distal portion 102b, and an optional grip 103 extending radially outwardly from the distal portion 102b. The injector 100 can further include a needle 110 at the distal portion 102b of the container 102, a plunger 104 configured to be slidably positioned within a portion of the container 102, and a stabilizer 120 at a distal portion of the container 102. In some embodiments, the injector 100 includes a needle cap (not shown). The plunger 104 can include a rod 106 and a piston fixed to a distal end of the rod 106. A proximal portion of the plunger 104 can include a grip 107 extending radially outwardly from the plunger 104.

The container 102 can include a generally cylindrical sidewall defining a lumen therethrough. In other embodiments, the container 102 can have other suitable shapes. The container 102 can be configured to flex or bend outwardly away from a longitudinal axis of the injector 100 in response to one or more forces. For example, the material and/or wall thickness of the container 102 can be selected to impart a desired degree of flexibility to the container 102. In some embodiments, the container 102 can be made of a flexible polymer, such as silicone. In other embodiments, the container 102 can be made of other suitable materials.

In some embodiments, the plunger 104 is configured to flex or bend outwardly away from a longitudinal axis of the injector 100. In other embodiments, the plunger 104 is generally rigid and is not configured to flex or bend along its length.

FIG. 2 is an end view of the stabilizer 120 isolated from the rest of the injector 100. The stabilizer 120 can include a generally cylindrical hub 124 and one or more fins or flaps extending outwardly from the hub 124. For example, in the embodiment shown in FIG. 2, the stabilizer 120 includes a first flap 122a, a second flap 122b, and a third flap 122c. The first and third flaps 122a, 122c can be positioned at circumferentially opposing portions of the hub 124 such that the first flap 122a extends away from the hub 124 at an angle that is about 180 degrees from the direction at which the third flap 122c extends away from the hub 124. In other embodiments, the first and third flaps 122a, 122c can be positioned at other suitable angles with respect to one another. As further illustrated in FIG. 3, the stabilizer 120 includes a proximal surface 130a and a distal surface 130b generally opposite the proximal surface 130a. As shown in FIG. 3, in some embodiments one or more of the flaps 122 can be curved to accommodate the curvature at the injection site.

In some embodiments, the stabilizer 120 can be integral with the container 102. In other embodiments, the stabilizer 120 can be a separate component configured to be positioned around a distal region of the container 102. For example, in some embodiments the hub 124 includes a lumen 126 extending from the proximal surface 130a to the distal surface 130b and configured to receive a distal region of the container 102. The stabilizer 120 can have one or more coupling elements (not shown) configured to mate with one or more coupling elements on the container 102. In a particular embodiment, the stabilizer 120 can be integral with the needle 110. In other embodiments, the needle 110 is a separate component configured to releasably attach to the stabilizer 120 and/or the container 102.

In use, a user may take hold of the injector 100 with one hand by grasping the container 102 and/or one or more portions of the stabilizer 120. In some embodiments, the user may first fill the container 102 with a medicament (or other fluid). In other embodiments, the injector 100 can be pre-loaded with the medicament. Before or after grasping the injector 100, the user can use their other hand to stabilize the target injection site on the subject. For example, when the injector 100 is used for delivering a dose of medicine to a dog (e.g., insulin, etc.), a user can use their free hand to grab and pinch together the loose skin along the neck or back of the dog. The user can then insert the needle 110 into the skin, parallel to the fold of the skin such that the injected medicament is delivered subcutaneously. To deliver the medicament through the needle 110, the user depresses the plunger 104 with their thumb while grasping the stabilizer 120 with one or more fingers on the same hand as the thumb used to depress the plunger 104. This way, the user can have a free hand to stabilize the dog (or other live subject). In some situations, the user may stabilize the injector 100 with both hands while delivering the medicament. In either scenario, the injector 100 of the present technology flexes about its longitudinal axis (in any direction) in response to subject movement (as the stabilizer is held in place by the user), thereby allowing the subject to move during injection of the needle 110 and/or delivery of the medicament without disturbing the positioning of the needle 110 within the subject. In addition, the injector 100 of the present technology may help reduce the incidence of needle-stick injury/accidents because of the improved control of container 102 and needle 110.

From the foregoing, it will be appreciated that specific embodiments of the invention have been described herein for purposes of illustration, but that various modifications may be made without deviating from the scope of the invention. Accordingly, the invention is not limited except as by the appended claims.

Although the invention has been described in terms of particular embodiments and applications, one of ordinary skill in the art, in light of this teaching, can generate additional embodiments and modifications without departing from the spirit of or exceeding the scope of the exampled invention. Accordingly, it is to be understood that the drawings and descriptions herein are proffered by way of example to facilitate comprehension of the invention and should not be construed to limit the scope thereof.

I claim:

1. An injector for delivering a medication to a subject, the injector comprising:
    a flexible container configured to house the medication, the container including a proximal portion, a distal portion, a proximal opening at the proximal portion, a distal opening at the distal portion, and a tubular sidewall defining a lumen therethrough, wherein the lumen extends from the proximal opening to the distal opening, and wherein the container is configured to be positioned generally parallel to a longitudinal axis;
    a plunger configured to be slidably received within the lumen of the container, wherein the plunger comprises a piston and a rod, and wherein the plunger is configured to be inserted through the proximal opening of the container;
    a stabilizer at the distal portion of the container, wherein the stabilizer includes—
        a proximal surface adjacent to the distal portion of the container;
        a distal surface opposite the proximal surface and configured to be positioned adjacent to an exterior portion of the subject;
        a hub having a hub lumen extending therethrough from the proximal surface to the distal surface, wherein the hub lumen is in fluid communication with the lumen of the container;
        a first flap extending away from the hub in a first direction;
        a second flap extending away from the hub in a second direction;
        a third flap extending away from the hub in a third direction, and
    a needle coupled to the distal portion of the container and extending distally past the distal surface of the stabilizer, wherein the stabilizer is configured to be grasped by a user during the delivery of the medication from the container through the needle to the subject to secure the position of the needle within the subject as the subject moves, and wherein the container is configured to bend outwardly away from the longitudinal axis as the subject moves while the needle is within the subject.

2. The injector of claim 1 wherein the stabilizer is integral with the container.

3. The injector of claim 1 wherein the stabilizer and the container are separate components.

4. The injector of claim 1 wherein the stabilizer and the needle are separate components.

5. The injector of claim 1 wherein the needle is integral with the stabilizer.

6. The injector of claim 1 wherein the at least two of the first, second, and third flaps are positioned at circumferentially opposite portions of the hub.

7. The injector of claim 1 wherein the container is made of silicone.

8. The injector of claim 1 wherein the plunger is configured to flex or bend outwardly away from the longitudinal axis.

9. The injector of claim 1 wherein the distal surface is curved.

10. The injector of claim 1 wherein the distal surface is generally linear.

11. The system of claim 1 wherein the needle extends generally perpendicularly relative to the distal surface of the stabilizer.

12. A system for delivering a medication to an animal, the system comprising:
    an injector including—
        a flexible container configured to house the medication, the container including a proximal portion, a distal portion, a proximal opening at the proximal portion, a distal opening at the distal portion, and a tubular sidewall defining a lumen therethrough, wherein the lumen extends from the proximal opening to the distal opening, wherein the container is configured to be positioned generally parallel to a longitudinal axis;
        a plunger configured to be slidably received within the lumen of the container, wherein the plunger comprises a piston and a rod, and wherein the plunger is configured to be inserted through the proximal opening of the container;
        a needle coupled to the distal portion of the container; and
    a stabilizer configured to be detachably coupled to the distal portion of the container,
        wherein the stabilizer includes—
        a proximal surface configured to be adjacent to the distal portion of the container when the stabilizer is coupled to the container,
        a distal surface opposite the proximal surface and configured to be positioned adjacent to and facing an exterior portion of the animal while the needle is inserted into an interior portion of the animal and/or while the plunger is advanced within the container lumen to dispense the medication from the container through the needle, wherein the needle of the injector extends distally past the distal surface of the stabilizer, and
        a guide member projecting away from the proximal surface of the stabilizer, wherein the guide member is configured to be grasped by a user during the delivery of the medication to the animal to secure the position of the needle within the animal as the animal moves, and wherein the container is configured to bend outwardly away from the longitudinal axis along a length of the container between the proximal and distal portions as the animal moves while the needle is within the animal.

13. The system of claim 12 wherein the container is made of silicone.

14. The system of claim 12 wherein the plunger is configured to flex or bend outwardly away from the longitudinal axis.

15. The system of claim 12 wherein the distal surface is curved.

16. The system of claim 12 wherein the distal surface is generally linear.

17. The system of claim 12 wherein the stabilizer includes a stabilizer lumen extending continuously therethrough from the proximal surface to the distal surface, wherein the stabilizer lumen is in fluid communication with the lumen of the container.

\* \* \* \* \*